United States Patent
Choi et al.

(10) Patent No.: US 7,845,849 B1
(45) Date of Patent: Dec. 7, 2010

(54) TESTING BGA SOLDER JOINTS BY LOCALIZED PULSED-HEAT THERMOGRAPHY

(75) Inventors: Jae Choi, Westminster, CO (US); Mark Woolley, Broomfield, CO (US)

(73) Assignee: Avaya Inc., Basking Ridge, NJ (US)

( * ) Notice: Subject to any disclaimer, the term of this patent is extended or adjusted under 35 U.S.C. 154(b) by 405 days.

(21) Appl. No.: 12/103,389

(22) Filed: Apr. 15, 2008

(51) Int. Cl.
*G01K 1/00* (2006.01)
*G01N 25/00* (2006.01)

(52) U.S. Cl. .............................. 374/120; 374/5; 374/57; 374/141

(58) Field of Classification Search .............. 374/120, 374/57, 5, 141
See application file for complete search history.

(56) References Cited

U.S. PATENT DOCUMENTS

| | | | |
|---|---|---|---|
| 4,481,418 A | 11/1984 | Vanzetti et al. | |
| 4,792,683 A * | 12/1988 | Chang et al. | 250/341.6 |
| 5,984,522 A * | 11/1999 | Koizumi | 374/5 |
| 6,375,347 B1 * | 4/2002 | Bruce et al. | 374/5 |
| 6,585,146 B2 | 7/2003 | Shepard | |
| 6,847,900 B2 | 1/2005 | Ragland | |
| 2004/0028113 A1 * | 2/2004 | Schlagheck et al. | 374/57 |

OTHER PUBLICATIONS

Avdelidis, N.P. and Wallace, P., "Pulsed thermography in the investigation of PCBs for defect detection & analysis", 9 pp., NDT Group, TWI Technology Centre, South Wales, UK.

* cited by examiner

*Primary Examiner*—Lisa M Caputo
*Assistant Examiner*—Mirellys Jagan
(74) *Attorney, Agent, or Firm*—David Volejnicek

(57) ABSTRACT

A pulse of heat or cold is applied and conducted transversely through a ball grid array device and a printed circuit board via a selected one of the solder joints between them. Heat diffused through the other solder joints is neutralized by a thermal bias shield. The shield is then removed and a thermographic image of the printed circuit board is taken. The process is repeated for each solder joint, and the images are compared to identify defective solder joints.

26 Claims, 3 Drawing Sheets

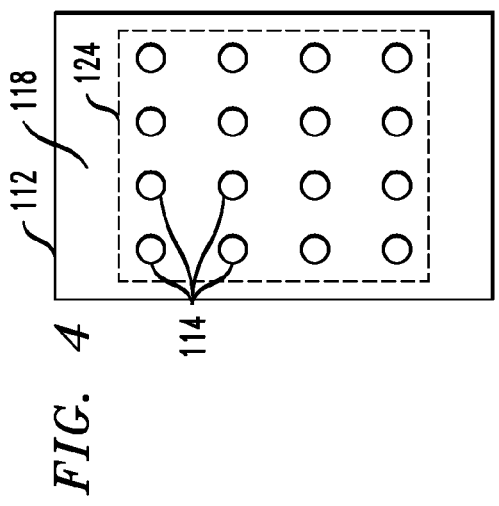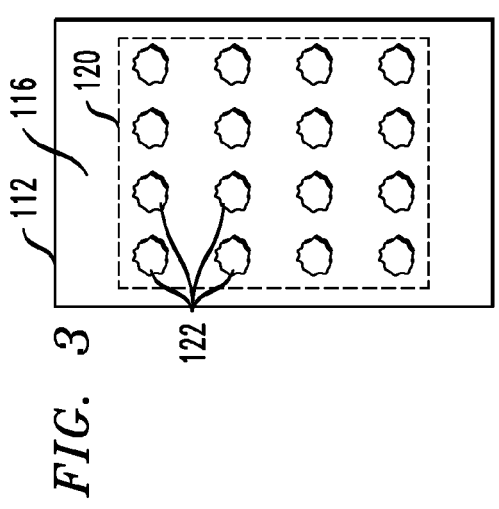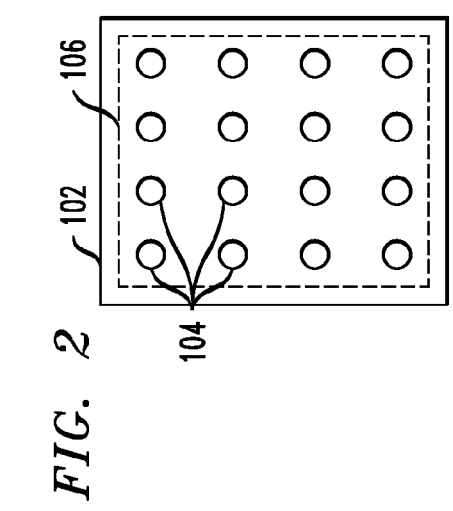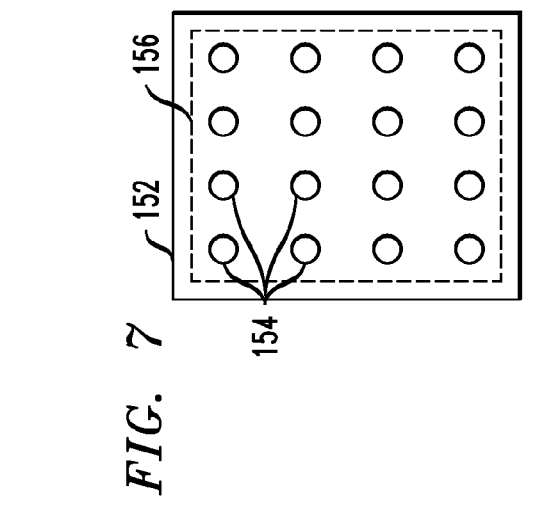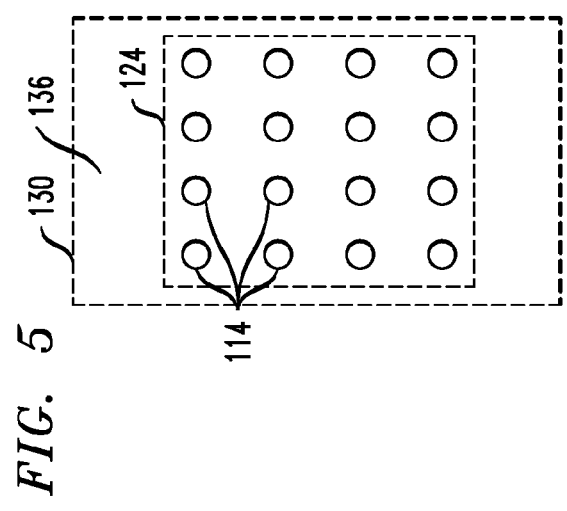

TESTING BGA SOLDER JOINTS BY LOCALIZED PULSED-HEAT THERMOGRAPHY

TECHNICAL FIELD

This invention relates generally to testing of electrical contacts and specifically to testing of solder joints.

BACKGROUND OF THE INVENTION

Ball-grid-array (BGA) devices use a grid array of solder balls to attach contacts of the BGA device to contacts of a printed-circuit (PC) board via reflow soldering. Bad connections are a common cause of failure, and therefore it is necessary to inspect and test the connections to ensure their good quality. But as the scale of device integration advances, the number of connections to a BGA device may number in the hundreds, resulting in their being separated from each other by mere microns of distance. This close spacing makes it difficult if not impossible to test the quality of these connections by using standard x-ray techniques. Furthermore, due to their placement between (under) the device and the PC board, most of the connections cannot be reached by probes. This makes it difficult if not impossible to test the connections by measuring their electrical resistance to signals. Also, many signals are buried within multi-layer PCB boards and hence are not available externally for testing purposes.

As a last resort, testers may use the "dye and pry" technique, which relies on a liquid dye to penetrate into microcracks or under open solder ball connections. After the dye dries, they pry the BGA off of the PCB, inspect the solder balls for the presence of the dye and investigate problems that the dye reveals. However, this method makes it difficult or impossible to identify the true root cause of contact failures due to damage to the boards during prying. It also destroys the circuit, and hence cannot be used to ensure good quality of circuits that are intended for use after testing.

Improved thermographic testing is a non-invasive and non-destructive test method that uses thermography cameras to detect thermal anomalies, called "hot spots," which often precede, and hence portend, equipment failure. Pulsed heat technology applies and concentrates a high-energy pulse of heat at an application point. These techniques have been used together to evaluate spot welds between joined materials such as pieces of metal (U.S. Pat. No. 6,585,146), and to inspect exposed (not covered) solder joints (U.S. Pat. Nos. 4,481,418 and 4,792,683). But, to the inventors' knowledge, it has heretofore not been known how to adapt these techniques for testing of solder joints between electronic devices, such as BGA devices, and PWBs where the solder joints are hidden from view and access (covered).

SUMMARY OF THE INVENTION

According to one aspect of the invention, solder joints between a ball grid array device and a circuit board are evaluated as follows. Heat or cold is applied to the device opposite at least one of the solder joints. At least some of the applied heat or cold that is conducted transversely through the device and the board via the at least one solder joint is allowed to appear on the board, but appearance of the rest of the applied heat or cold on the board is substantially neutralized. The transversely-conducted heat or cold is then imaged on the board. Advantageously, the image can be analyzed to determine if the selected solder joint is defective.

According to another aspect of the invention, the evaluation is effected as follows. A pulse of heat is applied to a first surface of the device. The pulse is focused on a first portion of the first surface. The first surface is opposite to a second surface of the device that bears the solder joints. The first portion is opposite to an individual one of the solder joints. A second portion, except for a third portion, of a first surface of the board is thermally biased to substantially neutralize (e.g., even out) a temperature of the second portion except for the third portion. The first surface of the board is opposite to a second surface of the board to which the device is attached, the second portion is opposite to the device, and the third portion is opposite to the individual one of the solder joints. The thermal biasing is then ceased, and at least the first portion of the second portion is thermographically imaged.

The invention may be implemented either as a method or an apparatus that effects the method.

BRIEF DESCRIPTION OF THE DRAWING

These and other features and advantages of the invention will become more apparent from considering the following description of an illustrative embodiment of the invention together with the drawing, in which:

FIG. 2 is a frontal view of a pulsed-heat source of the system of FIG. 1;

FIG. 3 is a frontal view of the first side of a ball grid array device of the system of FIG. 1;

FIG. 4 is a frontal view of a second side of the ball grid array device of the system of FIG. 1;

FIG. 5 is a frontal view of a part of a first side of a printed circuit board of the system of FIG. 1;

FIG. 6 is a frontal view of a part of a second side of the printed circuit board of the system of FIG. 1;

FIG. 7 is a frontal view of a thermal bias shield of the system of FIG. 1.

DETAILED DESCRIPTION

Figure 1:
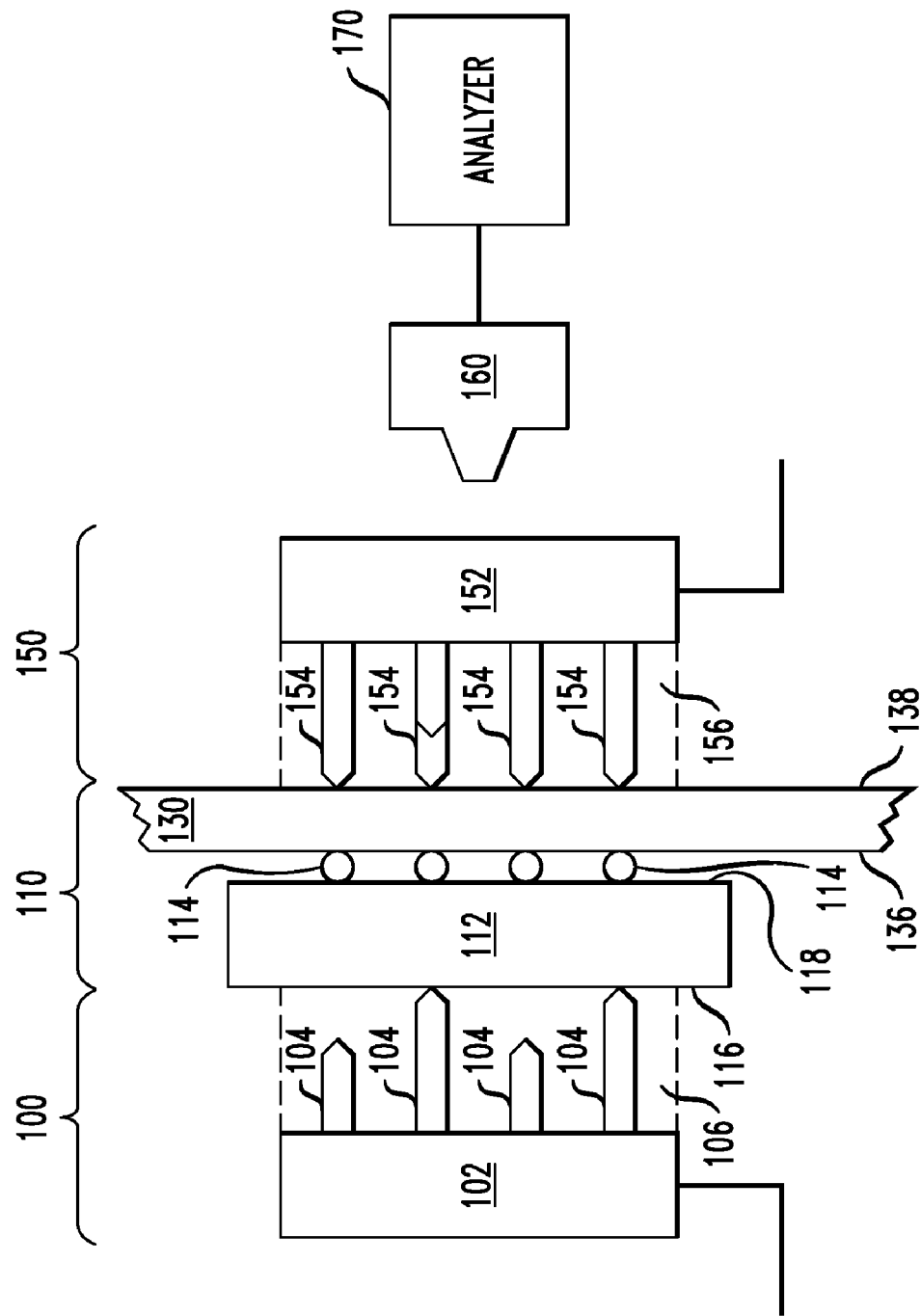
FIG. 1 is a block diagram of a system for evaluating solder joints between a ball grid array device and a printed circuit board.

FIG. 1 shows an illustrative system for testing solder joints, such as ball grid array device solder joints, by localized pulsed-heat thermography. Shown in this system is a circuit assembly 110 that is being tested, comprising a ball grid array (BGA) device 112 and a printed circuit board (PCB) 130 that are joined together by solder joints 114. The apparatus for testing solder joints 114 comprises a pulsed-heat source 100, a thermal bias shield 150, a thermographic imager 160, and an analyzer 170. Pulsed-heat source 100 comprises a generator 102 of a high-energy pulse of heat and a plurality of probes 104 for applying the pulse of heat to one or more selected application points. Pulsed-heat source 100 is illustratively a thermal heater, such as a Melcor 2CP085-100-31-20 device, for example. Alternatively, pulsed-heat source 100 may be a laser. In the case of source 102 being a heater, probes 104 are illustratively metallic probes made from a highly thermally-conductive material, such as beryllium. In the case of source 102 being a laser, probes 104 are optical fibers.

Thermal bias shield 150 thermally biases a portion of PCB 130 to substantially neutralize (e.g. even-out) the temperature thereof. Thermal bias shield 150 illustratively comprises a thermal cooler 152 and a plurality of probes 154 for making contact between cooler 152 and PCB 130 at one or more selected application points. Cooler 152 is illustratively the same device as the thermal heater of pulsed heat source 102, but is electrically biased oppositely to the thermal heater. Probes 154 are illustratively metallic probes made from a highly-thermally-conductive material, such as beryllium.

Thermographic imager 160 is illustratively a conventional thermographic camera. It is connected to an analyzer 170. Analyzer 170 may be as simple as a display for displaying the images captured by imager 160. Or, it may comprise a computer programmed with an analysis program for automatedly analyzing the captured images, such as a form of the system disclosed in U.S. Pat. No. 6,847,900, for example.

Solder joints 114 form an array 124 on a face 118 of BGA device 112, as shown in FIG. 4, and on a face 136 of PCB 130, as shown in FIG. 5. Preferably, probes 104 of pulsed-heat source 100 form a corresponding, matching, array 106, as shown in FIG. 2. When applied to a face 116 of BGA device 112, array 106 of probes 104 forms a corresponding array 120 of contact points 122, as shown in FIG. 3, that are located directly opposite solder joints 114 of array 124. Similarly, probes 154 of thermal bias shield 152 form an array 156 that corresponds to—matches—array 124 of solder joints 114, as shown in FIG. 7. When applied to face 138 of PCB 130, array 156 of probes 154 forms a corresponding array 140 of contact points 144, as shown in FIG. 6, that are located directly opposite solder joints 114 of array 124.

If heat cannot be delivered to selected individual probes 104, but is delivered to all probes 104 at the same time, then illustratively probes 104 of pulsed-heat source 100 are individually extendable to enable a selected one or more probes 104 to make one or more contacts 122 with surface 116 of BGA device 112, as shown in FIG. 1.

Probes 154 of thermal bias shield 150 are individually retractable (or alternatively removable) to enable only a selected one or more probes 154 to not make one or more contacts 144 with surface 138 of PCB 130, also as shown in FIG. 1. Probes 104 and 154 are operated in unison, such that when a probe 104 is either extended or selected to receive heat, the corresponding, oppositely-located, probe 154 is extended or retracted, likewise as shown in FIG. 1.

Figure 8:
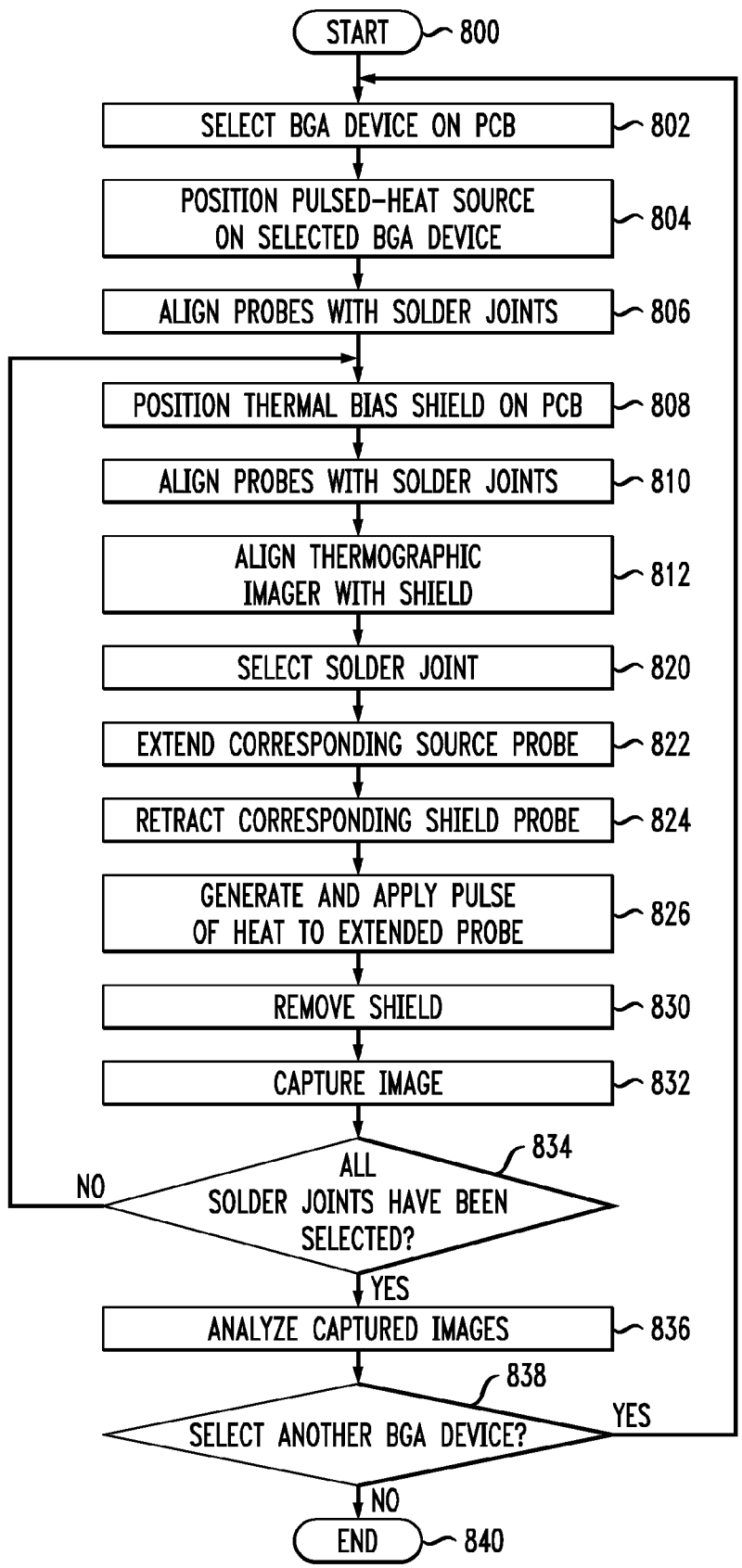
FIG. 8 is a flowchart of operation of the system of FIG. 1.

The operation of the system of FIG. 1 is illustrated in FIG. 8. At the start of testing, at step 800, a BGA device 112 on PCB 130 is selected, at step 802, pulsed-heat source 100 is positioned on the selected BGA device 112, at step 804, and its array 106 of probes 104 is aligned with (i.e., directly opposite) array 124 of solder joints 114, at step 806. Also, thermal bias shield 150 is positioned on PCB 130, at step 808, and its array 156 of probes 154 is aligned with (i.e., directly opposite) array 124 of solder joints 114, at step 810. Thermographic imager 160 is then positioned over shield 150 so that it can image array 140 on PCB 130, at step 812. Next, one (or more) solder joint 114 is selected, at step 820, the corresponding probe 104 of source 100 is extended to make a contact 144 with surface 116 of BGA device 112, at step 822, and the corresponding, opposite, probe 154 of shield 150 is retracted, at step 824. Generator 102 then generates a pulse of heat, and the extended probe 104 applies the pulse to surface 116 of BGA device 112, at step 826.

The heat propagates in all directions in the circuit assembly 110, but the shortest propagation distance to surface 138 of PCB 130 is directly, transversely, through assembly 110. Consequently, more of the heat can be expected to be conducted by the selected solder joint 114 and to appear at probe 154 that is opposite the extended probe 104 and the selected solder joint 114 than at any other probe 154. Nevertheless, probes 154 of shield 150 are used to conduct the diffused heat away from PCB 130, while retracted probe 154 enables the directly transversely-conducted heat to appear on surface 138 of PCB 130.

Shield 150 is now withdrawn, at step 830, thus exposing array 140 on PCB 130 to imager 160, and imager 160 captures its image, at step 832.

If all solder joints 114 have not yet been selected, as determined at step 834, the system of FIG. 1 returns to step 808 to repeat the process for another selected solder joint 114. If all solder joints 114 have been selected, analyzer 170 analyzes the captured images to determine whether any of solder joints 114 are defective, at step 836. For example, the captured images are compared to determine whether any image corresponding to a selected solder joint 114 shows less heat at area 144 that corresponds to the selected solder joint 114 than the other images show for their corresponding solder joints 114. If so, then the selected solder joint 114 is likely to be defective.

After the testing of solder joints 114 of BGA device 112 is completed, a determination is made of whether solder joints of another BGA device are to be tested, at step 838. If so, the process returns to step 802; if not, the process ends, at step 840.

Of course, various changes and modifications to the illustrative embodiment described above will be apparent to those skilled in the art. For example, in an alternative embodiment, thermal bias shield 110 illustratively comprises a thermal cooler 152 and a cooling block 156 with the plurality of probes 154 movably positioned within holes in cooling block 156. Cooling block 156 is illustratively also made from a highly-thermally-conductive material, and provides cooling for the entire area 140 of FIG. 6 except one or more areas 144 that are not being contacted by probes 154.

In yet another embodiment, thermal bias shield 110 illustratively comprises thermal cooler 152 and cooling block 156 with holes therein instead of probes 154.

In yet another embodiment, array of probes 104 may be replaced by a thermally-conductive block 106 and array of probes 154 may be replaced by a thermally-conductive block 156, wherein imager 160 images the rise of heat over time at areas 144 of array 140 of FIG. 6 after shield 150 is removed.

In yet another embodiment, the thermal system is reversed such that generator 102 supplies cold and device 152 supplies a biasing heat, whereby analyzer 170 analyzes withdrawal of heat by solder joints 114 from face 138 of PC board 130 instead of supply of heat by solder joints 114 to face 138 of PC board 130.

In yet another embodiment, generator 102 may be a source of steady heat (or cold), as opposed to pulsed heat (or cold).

In yet another embodiment, shield 150 may be made from transparent or thermally transparent material, such as a polycarbonate or an acrylic polymer, whereby imager 160 may image array 140 on PCB 130 through shield 150, i.e., with shield 150 in place.

Such changes and modifications can be made without departing from the spirit and the scope of the invention and without diminishing its attendant advantages. It is therefore intended that such changes and modifications be covered by the following claims except insofar as limited by the prior art.

What is claimed is:

1. An apparatus for evaluating solder joints between a ball grid array device and a circuit board, comprising:

a source of heat or cold for applying the heat or the cold to the ball grid array device opposite at least one of the solder joints;

a thermal bias shield for allowing the applied heat or cold that is conducted transversely through the ball grid array device and the printed circuit board via the at least one solder joint to appear on the printed circuit board, and for substantially neutralizing appearance on the printed circuit board of at least the applied heat or cold other than the transversely-conducted heat or cold; and a thermographic imager for imaging the transversely-conducted heat or cold on the printed circuit board.

2. The apparatus of claim 1 wherein:
the source is adapted to apply a pulse of the heat or cold to the ball grid array device opposite a selected one of the solder joints.

3. The apparatus of claim 2 wherein:
the thermal bias shield is adapted to allow the transversely-conducted heat or cold to appear on the printed circuit board while the thermal bias shield is in place.

4. An apparatus for evaluating solder joints between a ball grid array device and a circuit board, comprising:
means for applying a pulse of heat to the ball grid array device opposite a selected one of the solder joints;
means for allowing heat of the pulse that is conducted transversely through the ball grid array device and the printed circuit board via the selected solder joint to appear on the printed circuit board;
means for substantially neutralizing appearance on the printed circuit board of heat of the pulse other than the transversely-conducted heat; and
means for imaging the transversely-conducted heat on the printed-circuit board.

5. A method of evaluating solder joints between a ball grid array device and a circuit board, comprising:
applying heat or cold to the ball grid array device opposite at least one of the solder joints;
substantially neutralizing appearance on the printed circuit board of at least the applied heat or cold other than the applied heat or cold that is conducted transversely through the ball grid array device and the printed circuit board via the at least one solder joint;
allowing the transversely-conducted heat or cold to appear on the printed circuit board; and
imaging the transversely-conducted heat or cold on the printed-circuit board.

6. The method of claim 5 wherein:
applying comprises
applying a pulse of the heat or cold to the ball grid array device opposite a selected one of the solder joints.

7. The method of claim 6 wherein:
substantially neutralizing comprises
substantially allowing the transversely-conducted heat or cold to appear on the printed circuit board while the applied heat or cold other than the transversely-conducted heat or cold is being neutralized.

8. An apparatus for evaluating solder joints between a ball grid array device and a circuit board, comprising:
a pulsed-heat source for applying, to a first surface of the device, a pulse of heat that is focused on a first portion of the first surface, wherein the first surface is opposite to a second surface of the device that bears the solder joints and the first portion is opposite to an individual one of the solder joints;
a thermal bias shield for selectively thermally biasing a second portion, except for a third portion, of a first surface of the board to substantially neutralize a temperature of the second portion except for the third portion, wherein the first surface of the board third surface is opposite to a second surface of the board to which the device is attached, the second portion is opposite to the device, and the third portion is opposite to the individual one of the solder joints; and
a thermographic imager for thermographically imaging at least the third portion of the second portion when the thermal bias shield ceases the biasing.

9. The apparatus of claim 8 wherein the thermal shield is removable, and the camera is adapted for imaging the third portion when the shield is removed.

10. The apparatus of claim 8 further comprising:
a device for evaluating the thermographic image.

11. The apparatus of claim 8 wherein:
neutralizing the temperature comprises evening out the temperature.

12. The apparatus of claim 8 wherein:
the thermographic imager comprises a thermographic camera.

13. The apparatus of claim 8 wherein:
the pulsed-heat source comprises
a generator of the pulse of heat; and
a probe for applying the pulse of heat to the first portion.

14. The apparatus of claim 13 wherein:
the probe comprises an optical fiber.

15. The apparatus of claim 13 wherein:
the probe is metallic.

16. The apparatus of claim 13 wherein:
the probe comprises beryllium.

17. The apparatus of claim 8 wherein:
the pulsed-heat source comprises
a generator of the pulse of heat; and
a first array of probes that substantially matches an array of the solder joints, each probe for selectively coupling the pulse of heat to the first portion of the first surface that is opposite to a solder joint corresponding to said probe.

18. The apparatus of claim 17 wherein:
the generator comprises
a thermoelectric heater; and
the probes extend outwardly from the thermoelectric heater.

19. The apparatus of claim 17 wherein:
the probes are individually moveable, and the source is adapted to move one of the probes into contact with the first surface at any one time to deliver the pulse of heat to only the first portion of the first surface that is opposite to the solder joint corresponding to the one probe.

20. The apparatus of claim 19 wherein:
the thermal bias shield comprises
a second array of individually-moveable probes that substantially matches the first array, each probe of the second array for selectively thermally biasing a third portion of the second portion of the first surface of the board that is opposite to a solder joint corresponding to said probe of the second array; wherein
the thermal bias shield is adapted to move one of the probes of the second array out of contact with the third surface to avoid biasing a third portion of the second portion of the first surface of the board that is opposite to a solder joint corresponding to the one of the probes of the second array, and
the thermal bias shield and the pulsed heat source are adapted to cooperate such that, for at least a portion of a time that a probe of the first array that corresponds to an individual solder joint contacts the first surface of the device, a probe of the second array that corresponds to the individual solder joint does not contact the first surface of the board.

21. The apparatus of claim 17 wherein:
the thermal bias shield comprises a second array of probes that substantially matches the first array, each probe of the second array for selectively thermally biasing a third portion of the second portion of the first surface of the board surface that is opposite to a solder joint corresponding to said probe of the second array.

22. The apparatus of claim 21 wherein:
the probes of the second array are metallic.

23. The apparatus of claim 21 wherein:
the probes comprise beryllium.

24. The apparatus of claim 21 wherein:
the probes of the second array are individually moveable, and the thermal bias shield is adapted to move one of the probes of the second array out of contact with the first surface of the board to cease biasing the third portion of the second portion of the first surface of the board that is opposite to a solder joint corresponding to the one of the probes of the second array.

25. The apparatus of claim 24 wherein:
the thermal bias shield further comprises
a thermoelectric cooler; and
the probes of the second array extend outwardly from the thermoelectric cooler.

26. A method for evaluating solder joints between a ball grid array device and a circuit board, comprising:
applying, to a first surface of the device, a pulse of heat that is focused on a first portion of the first surface, wherein the first surface is opposite to a second surface of the device that bears the solder joints and the first portion is opposite to an individual one of the solder joints;
thermally biasing a second portion, except for a third portion, of a first surface of the board to substantially neutralize a temperature of the second portion except for the third portion, wherein the first surface of the board is opposite to a second surface of the board to which the device is attached, the second portion is opposite to the device, and the third portion is opposite to the individual one of the solder joints;
ceasing the thermal biasing; and
following the ceasing, thermographically imaging at least the third portion of the second portion.

* * * * *